(12) United States Patent
Delso et al.

(10) Patent No.: US 8,718,232 B2
(45) Date of Patent: May 6, 2014

(54) RECONSTRUCTION OF AN EMISSION TOMOGRAPHY IMAGE

(75) Inventors: Gaspar Delso, Munich (DE); Ralf Ladebeck, Erlangen (DE); Axel Martinez-Möller, Munich (DE); Sibylle Ziegler, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 1136 days.

(21) Appl. No.: 12/626,127

(22) Filed: Nov. 25, 2009

(65) Prior Publication Data
US 2010/0278406 A1 Nov. 4, 2010

Related U.S. Application Data

(60) Provisional application No. 61/174,094, filed on Apr. 30, 2009.

(51) Int. Cl.
*A61B 6/03* (2006.01)

(52) U.S. Cl.
CPC ........................................ *A61B 6/03* (2013.01)
USPC ........................................................ 378/131

(58) Field of Classification Search
USPC ................... 250/363; 324/307–318; 382/131; 600/407–431; 378/4–20
See application file for complete search history.

(56) References Cited

U.S. PATENT DOCUMENTS

| | | | |
|---|---|---|---|
| 5,959,300 A * | 9/1999 | Hines et al. | 250/363.09 |
| 6,339,652 B1 * | 1/2002 | Hawkins et al. | 382/131 |
| 2003/0004405 A1 * | 1/2003 | Townsend et al. | 600/407 |
| 2003/0216631 A1 * | 11/2003 | Bloch et al. | 600/407 |
| 2004/0030246 A1 * | 2/2004 | Townsend et al. | 600/427 |
| 2004/0196960 A1 * | 10/2004 | Tanigawa et al. | 378/207 |
| 2007/0102641 A1 | 5/2007 | Schmand et al. | |
| 2008/0285828 A1 * | 11/2008 | Gagnon et al. | 382/131 |
| 2011/0058722 A1 * | 3/2011 | Hu et al. | 382/131 |

FOREIGN PATENT DOCUMENTS

WO   WO 2007052211 A1 *  5/2007

OTHER PUBLICATIONS

Delso et al., "Auswertung des Einflusses eines verminderten Sichtfeldes in der MR/PET Schwächungskorrektur", Presented Apr. 25, 2008, NuklearMedizin 2008—46. Jahrestagung der Deutschen Gesellschaft für Nuklearmedizin e.V., Abstract No. V146, pp. A 62-A 63.*
USPTO translation document No. 13/1783 of Delso et al.*
Tai et al., "A Hybrid Attenuation Correction Technique to Compensate for Lung Density in 3-D Total Body PET", 1996, IEEE Transactions on Nuclear Science, vol. 43, No. 1, pp. 323-330.*

(Continued)

*Primary Examiner* — Toan Ton
*Assistant Examiner* — John Corbett
(74) *Attorney, Agent, or Firm* — Harness, Dickey & Pierce, P.L.C.

(57) ABSTRACT

A method and an system are disclosed for reconstructing an emission tomography image in a combined MR (magnetic resonance) and emission tomography imaging system. In at least one embodiment, the method includes obtaining an MR image of a subject, the subject being clipped in the MR image; obtaining raw emission tomography scan data of the subject; determining a missing part of the subject clipped in the MR image; using information of the MR image and the determined missing part to obtain a final attenuation model of the subject; and reconstructing the emission tomography image using the raw data and the final attenuation model.

18 Claims, 7 Drawing Sheets

(56) References Cited

OTHER PUBLICATIONS

MR-PET:Combining Function,Anatomy, and More Schwaiger et al.; Others; 2005; DE.

Gaspar Delso et al.: "Impact of limited MR field-of-view in simultaneous PET/MR acquisition", The Journal of Nuclear Medicine, 49:162P, Jun. 14-18, 2008 http://jnumedmtg.snmjournals.org/cgi/content/meeting_abstract/49/MeetingAbstracts . . . .

* cited by examiner

RECONSTRUCTION OF AN EMISSION TOMOGRAPHY IMAGE

PRIORITY STATEMENT

The present application hereby claims priority under U.S.C. §119(e) on U.S. Provisional patent application No. 61/174,094 filed Apr. 30, 2009, the entire contents of which are hereby incorporated herein by reference.

FIELD

At least one embodiment of the present invention generally relates to a method and/or a system of reconstructing an emission tomography image in a combined MR (magnetic resonance) and emission tomography imaging system.

BACKGROUND

In an emission tomography system, photons from the inside of a body, or in case of system tune-up, from a phantom and the like that is to be imaged are detected. These photons pass from the interior of the body to a detector outside the body and may be attenuated by different parts of the body, depending on the composition of the body. Generally, the emission tomography may be a Positron Emission Tomography (PET), a Single Photon Emission Computed Tomography (SPECT), and the like. In order to reconstruct a three-dimensional distribution of a radionuclide within the body or phantom accurately, this attenuation must be considered.

In a combined MR (magnetic resonance) and emission tomography imaging system, a subject may not be imaged entirely in a MR image due to technical limitations of the system and thus, the subject is clipped in the MR image. Therefore, the attenuation imposed by the body of the subject may not be considered accurately while reconstructing the emission tomography image, and thus, the emission tomography image may not be accurate.

SUMMARY

In at least one of the embodiments of the invention, an emission tomography image is reconstructed more accurately in a combined MR and emission tomography imaging system.

A method of reconstructing an emission tomography image in a combined MR (magnetic resonance) and emission tomography imaging system are disclosed.

The subject comprises a first part that lies in the field of view of an MR scanner and a second part that lies outside the field of view. In an MR image, the second part is thus clipped, i.e. the MR image does not have image information about the second part. Determining the missing parts of the subject clipped in the MR image, and thereafter, using the information of the missing parts and the MR image to obtain a final attenuation model to be used for reconstructing the final emission tomography image enables in an accurate reconstruction of the emission tomography image. The information of the missing parts enable in considering the attenuation of the parts of the subject clipped in the MR image. Thus, in at least one embodiment, the attenuation induced by the entire body of the subject may be considered while reconstructing the emission tomography image.

According to another embodiment, the determining of the missing part includes using the raw emission tomography scan data. The using of the raw emission tomography scan data to determine the missing parts of the subject in the MR image eliminates or at least reduces the requirement of additional devices to image the subject entirely.

According to another embodiment, the using of the raw emission tomography scan data to obtain the missing part of the subject may comprise using the raw emission tomography scan data to reconstruct a first non-perfect emission tomography image without attenuation correction and obtaining the missing part from the first non-perfect emission tomography image. The first non-perfect emission tomography image does reflect the geometry of the subject correctly, but it may serve to retrieve information about patient geometry for determining missing parts of the subject. The raw emission tomography scan data may be used to reconstruct a non-perfect emission tomography image and obtain the missing parts from the non-perfect emission tomography image. The non-perfect emission tomography image is reconstructed without performing an attenuation correction.

According to yet another embodiment, the obtaining of the missing part may include segmenting a profile of the subject reconstructed in the first non-perfect emission tomography image. Segmentation of the profile of the subject enables in identifying the missing parts of the subject in the MR image. Segmentation helps to retrieve geometry information of the subject from the first non-perfect emission tomography image.

According to yet another embodiment, the segmentation may be performed using a 3d deformable surface model.

According to yet another embodiment, the method may further comprise using the first non-perfect emission tomography image to adapt synthetic data to the profile of the subject in the MR image. As the first non-perfect emission tomography image provides information of parts not within the field of view of the MR scanner, this helps in adapting synthetic data to the profile of the subject of the MR image.

According to yet another embodiment, the synthetic data is a phantom data.

According to yet another embodiment, the using of the raw emission tomography scan data to obtain the missing part of the subject may comprise using the raw emission tomography scan data to reconstruct a first emission tomography image with a first attenuation correction model, and obtaining the missing part from the first emission tomography image.

The first attenuation correction model is an imperfect model that reflects the actual attenuation of the subject only partially. In particular, the first imperfect attenuation model reflects attenuation correction of the part of the subject that is located within the field of view of the MR scanner more correctly than that of a part of the subject that is outside the field of view. For example, the attenuation correction of the subject within the field of view of the MR scanner is more accurate than the part of the subject outside the field of view of the MR scanner as the information of the parts outside the field of view of the MR scanner is not known from the MR image.

The raw emission tomography scan data may be used to reconstruct a first emission tomography image with a first attenuation correction model and obtain the missing parts from the first emission tomography image. The first emission tomography image is reconstructed by performing an attenuation correction using the first attenuation correction model. This enables in reconstructing the first emission tomography image by performing an attenuation correction on the raw emission tomography scan data.

The first emission tomography image does not reflect the profile of the subject accurately. However, the first emission tomography image may depict the profile of the subject relatively more correct and may be used to retrieve information about subject geometry for determining missing parts of the subject.

According to yet another embodiment, the obtaining of the missing part includes segmenting a profile of the subject reconstructed in the first emission tomography image. Segmentation of the profile of the subject enables in identifying the missing parts of the subject in the MR image According to yet another embodiment, the segmentation is performed using a 3d deformable surface model.

According to yet another embodiment, the first attenuation correction model uses information of the MR image. The first attenuation correction model may use the attenuation information provided by the MR image. For example, the first attenuation correction model may use the attenuation information of the profile of the subject clipped in the MR image. Advantageously, the first attenuation correction model may use the information of the MR image and synthetic data. The synthetic data may be phantom data or an attenuation map and the like.

According to yet another embodiment, the first attenuation correction model is solely based on information of the MR image. The first attenuation correction model may be based solely on the information of the MR image. Thus, the first attenuation correction model is based solely on the non-clipped part of the subject of the MR image and the clipped part of the subject is ignored for correction of the attenuation.

According to yet another embodiment, the first attenuation correction model is based on information of the MR image and a first estimation of a missing part, the first estimation of the missing part being independent from the raw emission tomography scan data. The first estimation of the missing parts may be a rough estimation of the missing parts of the subject. Thereafter, the first estimation of the missing parts may be used with information of the MR image to determine the first attenuation correction model.

According to yet another embodiment, the method may further comprise using the first emission tomography image to adapt synthetic data to the profile of the subject in the MR image. As the first emission tomography image provides information of parts not within the field of view of the MR scanner, this helps in adapting synthetic data to the profile of the subject of the MR image.

According to yet another embodiment, the synthetic data is a phantom data.

Another embodiment includes, a combined MR (magnetic resonance) and emission tomography imaging system.

BRIEF DESCRIPTION OF THE DRAWINGS

Embodiments of the present invention are further described hereinafter with reference to illustrated embodiments shown in the accompanying drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

Figure 1:
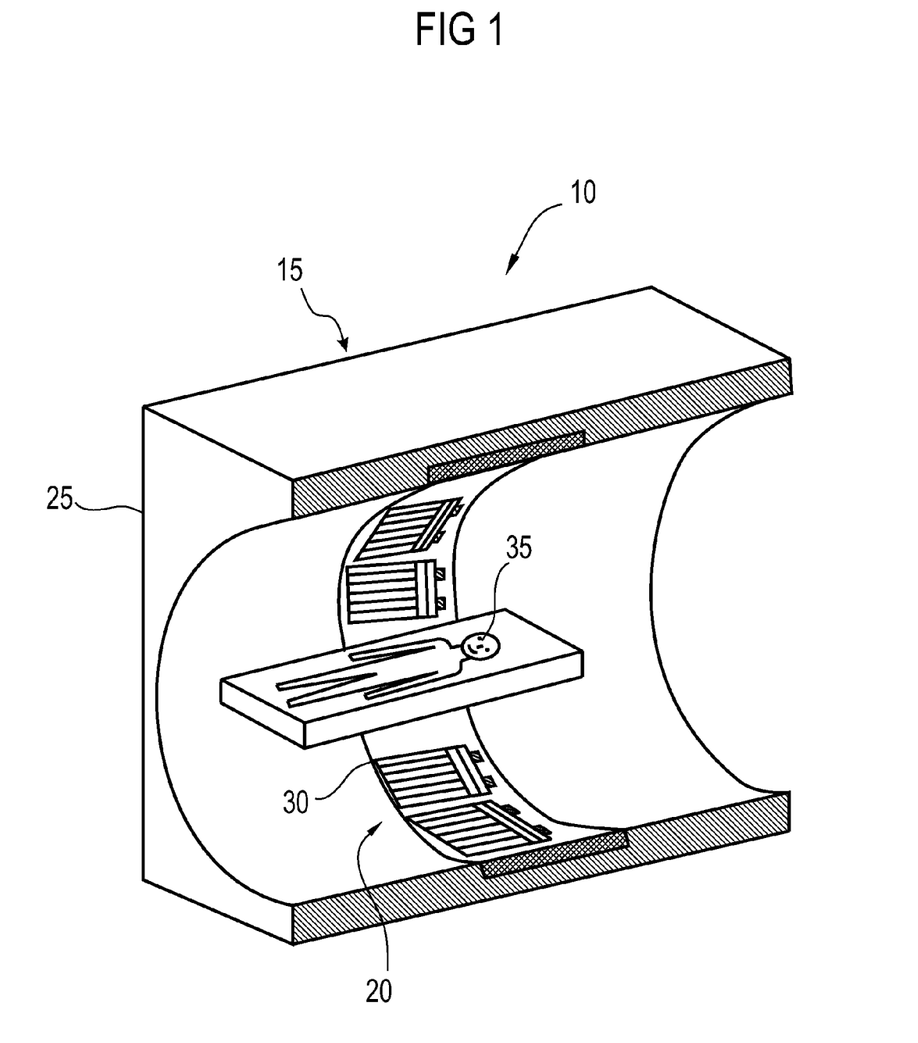
FIG. 1 illustrates an example of a combined MR and emission tomography imaging system according to an embodiment herein.

Referring to FIG. 1, a combined MR and emission tomography imaging system is illustrated according to an embodiment herein. The combined MR and emission tomography imaging system 10 comprises a MR scanner 15 and an emission tomography subsystem 20. The MR scanner 15 comprises a magnet system 25 for inducing a magnetic field for MR imaging. A ring 30 of the emission tomography subsystem 20 is disposed within the magnet system 25 of the MR scanner 15. For example, the ring 30 may be dimensioned such that the ring 30 may be positioned within the geometry of the MRI scanner 15. The ring 30 may comprise one or more detector modules to detect one or more photons. A subject 35 to be imaged is positioned into the space defined by the MRI scanner 15 and the emission tomography subsystem 20.

Figure 2:
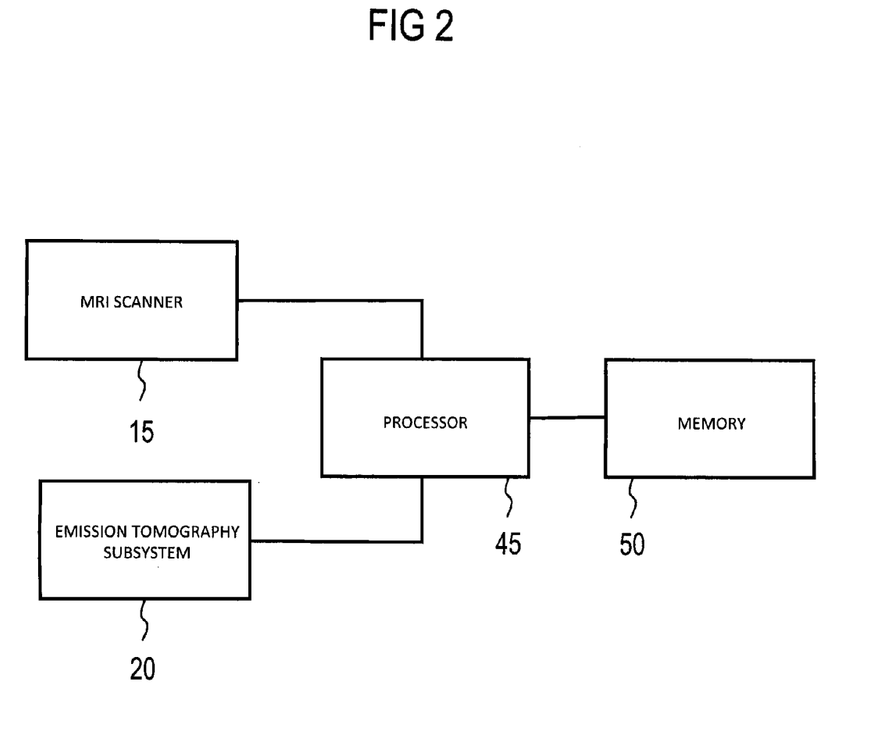
FIG. 2 illustrates a functional block diagram of a combined MR and emission tomography imaging system 10 according to an embodiment herein.

FIG. 2 illustrates a functional block diagram of a combined MR and emission tomography imaging system 10 according to an embodiment herein. The MR scanner 15 and the emission tomography subsystem 20 are operatively coupled to a processor 45. The processor 45 is operatively coupled to a memory 50. The memory 50 may include a semiconductor or solid state memory, magnetic tape, or removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 3A:
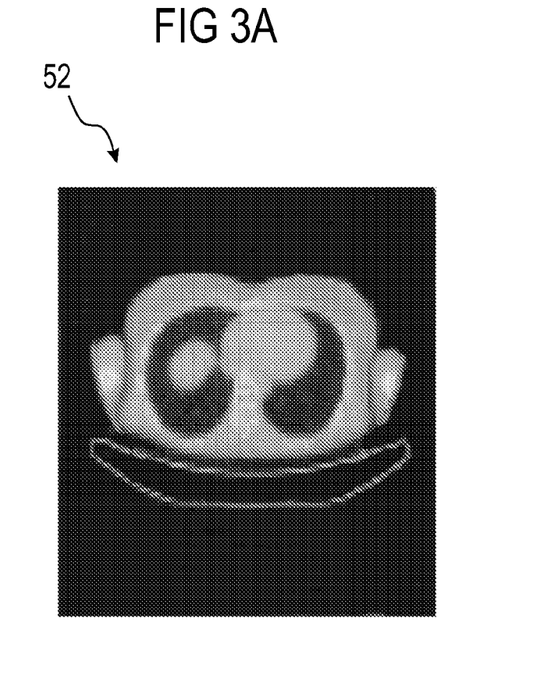
FIG. 3a illustrates a subject in an expected field of view of a MR scanner according to an embodiment herein.

FIG. 3a illustrates the subject 35 in an expected field of view of a MR scanner according to an embodiment. The image illustrated in FIG. 3a is obtained using a combined CT and emission tomography system as a combined MR and emission tomography system does not exist at present. The image of FIG. 3a has been clipped to illustrate the expected field of view of the MR scanner 15 of FIG. 1. For understanding purposes, the image of FIG. 3a shall be referred hereinafter as the MR image 52.

Referring now to FIG. 3a and FIG. 1, in accordance with an embodiment of the invention, an MR image 52 of the subject 35 is obtained by positioning the subject 35 in the field of view of the MR scanner 15 of the combined MR and emission tomography imaging system 10. Advantageously, the subject 35 may be positioned within the homogeneity volume of the magnetic field of the MR magnet system 25 as the magnetic field is more uniform within the homogeneity volume. The MR image 52 does not depict the complete profile of the subject 35 as some parts of the subject 35 are clipped in the MR image 52.

Figure 3B:
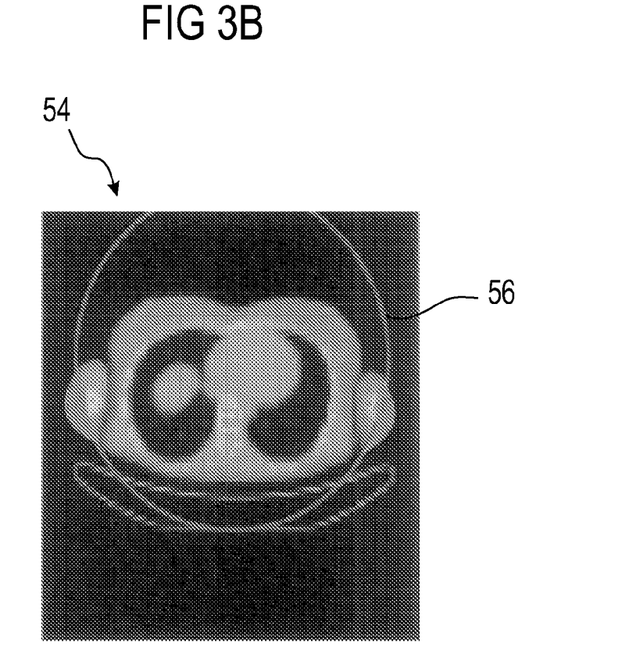
FIG. 3b illustrates an example of a CT image of a subject.

FIG. 3b illustrates an image 54 of the subject depicting a profile of the subject substantially. The image 54 is obtained using a combined CT and emission tomography imaging system and is illustrated for understanding purposes. Typically, an expected field of view of the combined MR and emission tomography imaging system 10 is limited as illustrated by the circle 56. Therefore, the subject in the MR image obtained using the combined MR and emission tomography imaging system 10 may be clipped. Thus, the MR image 52 typically depicts the profile of the subject 35 within the field of view of the MR scanner 15, i.e., the circle 56. Thus, the MR image 52 of FIG. 3a depicts the non clipped parts of the subject 35.

Referring now to FIG. 1, FIG. 2 and FIG. 3a, the MR scanner 15 may provide the MR image 52 to the processor 45. Advantageously, the processor 45 may store the MR image 52 at the memory 50 and may be retrieved by the processor 45 when desired. In an embodiment, raw emission tomography scan data may be used to determine the missing parts of the subject 35 in the MR image 52. Using raw emission tomography scan data to determine the missing parts of the subject outside the field of view of the MR scanner 15 eliminates the requirement of using external devices to image the entire profile of the subject. Accordingly, raw emission tomography scan data of the subject 35 is obtained from the emission tomography subsystem 20 of the combined MR and emission tomography imaging system 10. However, in alternative embodiments, the missing parts of the subject 35 in the MR image 52 may be determined using mechanical devices, cameras, laser, external radiation sources and the like. The emission tomography subsystem 20 may provide the raw emission tomography scan data to the processor 45 and the processor 45 may store the raw emission tomography scan data at the memory 50.

Figure 3C:
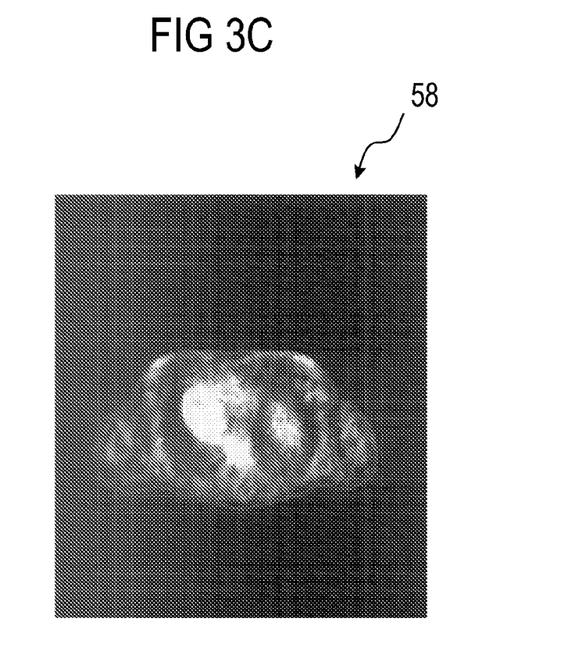
FIG. 3c illustrates an example of a first non-perfect emission tomography image according to an embodiment herein.

In accordance with one embodiment, the processor 45 may be adapted to use the raw emission tomography scan data to reconstruct a first non-perfect emission tomography image 58, as illustrated in FIG. 3c, without attenuation correction. The first non-perfect emission tomography image may depict a profile of the subject 35 substantially and not as clipped in the MR image 52 of FIG. 3a. However, as the first non-perfect emission tomography image 58 is reconstructed from the raw emission tomography scan data without performing any attenuation correction, the first non-perfect emission tomography image 58 may not depict the profile of the subject correctly, but may serve to obtain information of the profile of the subject for determining the missing parts of the subject 35.

In an embodiment, the first non-perfect emission tomography image 58 may be reconstructed with a larger field of view than required for the final reconstruction using data which is less reliable of low resolution at the borders.

Figure 3D:
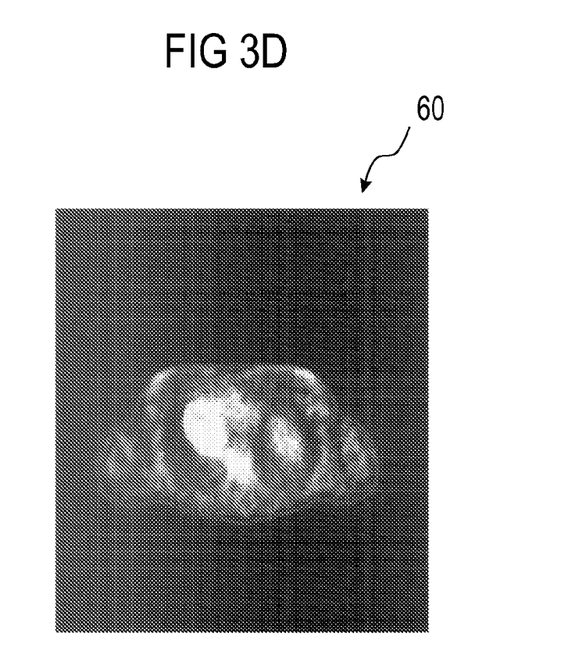
FIG. 3d illustrates an example of a first emission tomography image according to an embodiment herein.
Figure 3E:
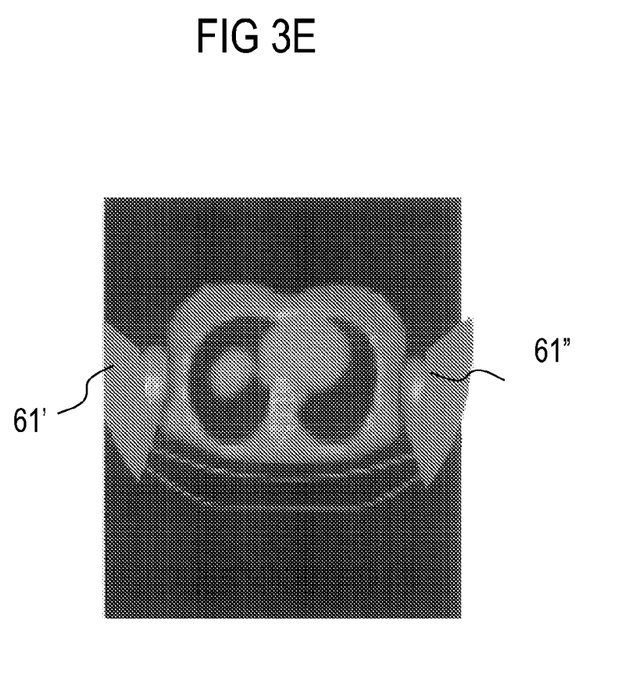
FIG. 3e illustrates a subject 35 of the MR image of FIG. 3a with boosted arm regions according to an embodiment herein.

Referring now to FIG. 1 and FIG. 2, alternatively, the processor 45 may be adapted to use the raw emission tomography scan data to reconstruct a first emission tomography image 60, as illustrated in FIG. 3d, with a first attenuation correction model. The first emission tomography image 60 may be an emission tomography image of the subject 35 reconstructed by performing attenuation correction using the first attenuation correction model. Thus, the first emission tomography image 60 may depict the profile of the subject substantially and not as clipped in the MR image 52. The profile depicted in the first emission tomography is relatively more correct. However, the profile of the subject depicted in the first emission tomography image 60 may not be perfect, but may serve to obtain information of the profile of the subject for determining the missing parts of the subject. For example, the first attenuation correction model may use the information of the MR image 52 OF FIG. 3a, or may be solely based on information of the MR image 52, or may be based on information of the MR image 52 and a first estimation of the missing parts of the subject 35, wherein the first estimation of the missing parts is independent from the raw emission tomography scan data. For example, the first attenuation correction model may use the information of the MR image 52 and synthetic data. However, the synthetic data may not be adapted to the profile of the subject in the MR image 52. In an embodiment, the synthetic data may be phantom data or an attenuation map, and the like. Additionally, the first estimation of the missing parts may be a rough estimation of the missing parts as illustrated in FIG. 3e. Referring now to FIG. 3e, the subject 35 of FIG. 1 in the MR image 52 of FIG. 3a is shown with boosted arm regions 61', 61". The boosted arm region 61', 61" correspond to the first estimation of the missing parts.

Referring again to FIG. 3d, the first attenuation correction model may be a rough estimation of the subject's attenuation which in turn may be used to obtain the first emission tomography image 60 of the subject 35. For example, the first attenuation correction model may be based on the attenuation of the MR image 520f FIG. 3a and the attenuation of the first estimation of the missing parts.

Referring now to FIG. 3c and FIG. 3d, the first non-perfect emission tomography image 58 of FIG. 3c and the first emission tomography image 60 of FIG. 3d may depict a profile of the subject 35 of FIG. 1 substantially and not as clipped in the MR image 52 of FIG. 3a. Thus, the first non-perfect emission tomography image 58 and the first emission tomography image 60 depicts the profile of the subject entirely including the parts outside the field of view of the MR scanner 15 of FIG. 1. However, their may be some differences between the profile of the subject 35 depicted in the first non-perfect emission tomography image 58 and the first emission tomography image 60 as the first emission tomography image 60 is reconstructed using a first attenuation correction model.

From the first non-perfect emission tomography image 58 or the first emission tomography image 60, the missing parts of the subject 35 of FIG. 1 may be determined, as the first non-perfect emission tomography image 58 and the first emission tomography image 60 depict the profile of the subject 35 substantially.

Referring now to FIG. 2, in an embodiment, the processor 45 may be adapted to segment the profile of the subject 35 of FIG. 1 from the first non-perfect emission tomography image 58 of FIG. 3c or the first emission tomography image 60 of FIG. 3d. Thereafter, missing parts of the subject 35 in the MR image 52 of FIG. 3a may be determined from the segmented profile of the subject depicted in either the first non-perfect emission tomography image 58 or the first emission tomography image 60. In an embodiment, the processor 45 may be adapted to compare the segmented profile of the subject 35 of the first non-perfect emission tomography image 58 or the first emission tomography image 60 with the MR image 52 to identify the missing parts. Advantageously, the profile of the subject 35 may be segmented from the first non-perfect emission tomography image 58 or the first emission tomography image 60 using a 3d deformable surface model.

Figure 3F:
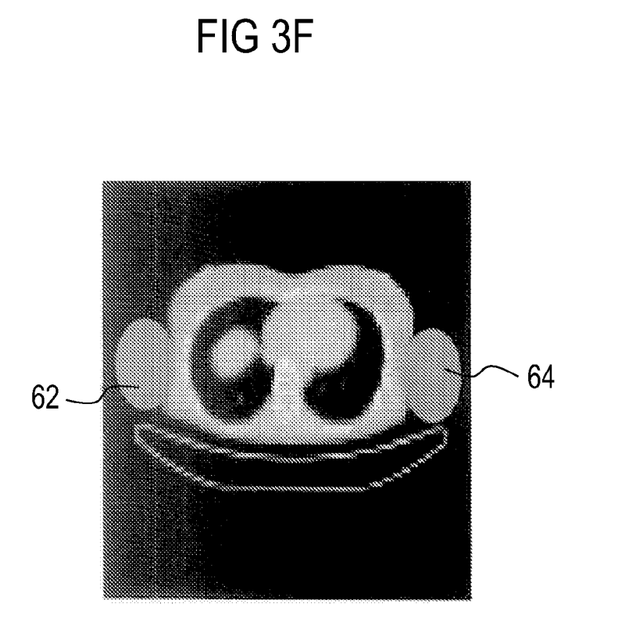
FIG. 3f illustrates the subject of the MR image of FIG. 3a in combination with synthetic elements corresponding to the missing parts according to an embodiment herein, FIG. 4 with reference to FIGS. 1 through 3f is a flow diagram illustrating a method of reconstructing an emission tomography image in a combined MR and emission tomography imaging system according to an embodiment herein.

The information of the missing parts of the subject 35 and the information of the subject 35 in the MR image 52 enable in obtaining a final attenuation model of the subject 35. Thereafter, a final emission tomography image of the subject 35 may be reconstructed using the raw emission tomography scan data and the final attenuation model. The final attenuation model of the subject 35, for example, may use the attenuation information of the MR image 52 and the attenuation of the missing parts. For an example, an incomplete attenuation model may be determined from the information of the MR image 52, and, thereafter, the incomplete attenuation model may be extended to the final attenuation model using the information of the missing parts. Referring now to FIG. 3f, in an embodiment, the information of the missing parts may be used to obtain the final attenuation model of the subject 35 of FIG. 1 by using synthetic data 62, 64 corresponding to the missing parts with the clipped subject 35 in the MR image 52 of FIG. 3a. The first non-perfect emission tomography image 58 of FIG. 3c or the first emission tomography image 60 of FIG. 3d information may be used to adapt the synthetic data to the profile of the subject in the MR image 52 of FIG. 3a. For an example, the synthetic data used may be phantom data aligned with the position of the missing parts in the MR image 52.

Thus, the final attenuation model obtained enables in reconstructing the final emission tomography using the raw emission tomography scan data with increased accuracy as more accurate attenuation of the missing parts of the subject in the MR image 40 is taken into consideration while reconstructing the final emission tomography image.

In an embodiment, the final emission tomography image may be used as the first emission tomography image to determine the missing parts and thereafter the subsequent final attenuation model in an iterative manner. The subsequent final attenuation model may then be used to reconstruct the subsequent final emission tomography image. Obtaining the subsequent final attenuation model and reconstructing the subsequent final emission tomography image in an iterative manner enables reconstructing a more accurate emission tomography image.

Figure 4:
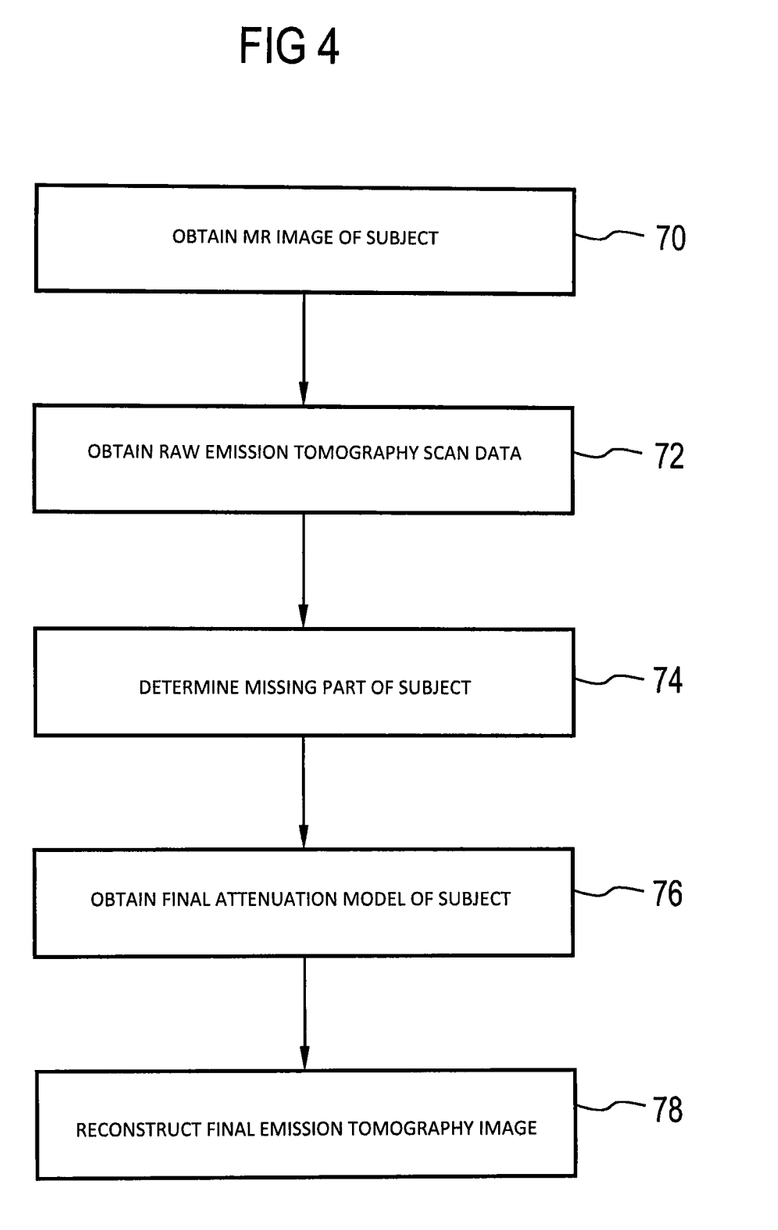

FIG. 4 with reference to FIGS. 1 through 3f is a flow diagram illustrating a method of reconstructing an emission tomography image in a combined MR and emission tomography imaging system according to an embodiment herein. At block 70, a MR image 52 of a subject 35 is obtained, wherein the subject 35 is clipped in the MR image 52. Next, at block 72, raw emission tomography scan data of the subject 35 are obtained. Moving next to block 74, a missing part of the subject 35 clipped in the MR image 52 is determined. At block 76, the information of the MR image 52 and the determined missing part are used to obtain a final attenuation model of the subject 35. Moving next to block 78, a final emission tomography image is reconstructed using the raw data and the final attenuation model.

Preferably, the determining of the missing part includes using the raw emission tomography scan data. Moreover, the using of the raw emission tomography scan data to obtain the missing part of the subject 35 may comprise using the raw emission tomography scan data to reconstruct a first non-perfect emission tomography image 58 without attenuation correction and obtaining the missing part from the first non-perfect emission tomography image 58. Moreover, the obtaining of the missing part includes segmenting a profile of the subject 35 reconstructed in the first non-perfect emission tomography image 58. Preferably, the segmentation is performed using a 3d deformable surface model.

Additionally, the first non-perfect emission tomography image 58 may be further used to adapt synthetic data to the profile of the subject in the MR image (52). Preferably, the synthetic data is a phantom data.

Additionally, the using of the raw emission tomography scan data to obtain the missing part of the subject 35 may comprise using the raw emission tomography scan data to reconstruct a first emission tomography image 60 with a first attenuation correction model, and obtaining the missing part from the first emission tomography image 60. Moreover, the obtaining of the missing part includes segmenting a profile of the subject 35 reconstructed in the first emission tomography image 60. Preferably, the segmentation is performed using a 3d deformable surface model. In an aspect, the first attenuation correction model may use information of the MR image 52. In another aspect, the first attenuation correction model may be solely based on information of the MR image 52. In yet another aspect, the first attenuation correction model is based on information of the MR image 52 and a first estimation of a missing part, the first estimation of the missing part being independent from the raw emission tomography scan data.

Moreover, the first emission tomography image 60 may be further used to adapt synthetic data to the profile of the subject in the MR image (52). Preferably, the synthetic data is a phantom data.

The embodiments herein can take the form of an entirely hardware embodiment, an entirely software embodiment or an embodiment including both hardware and software elements. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 5:
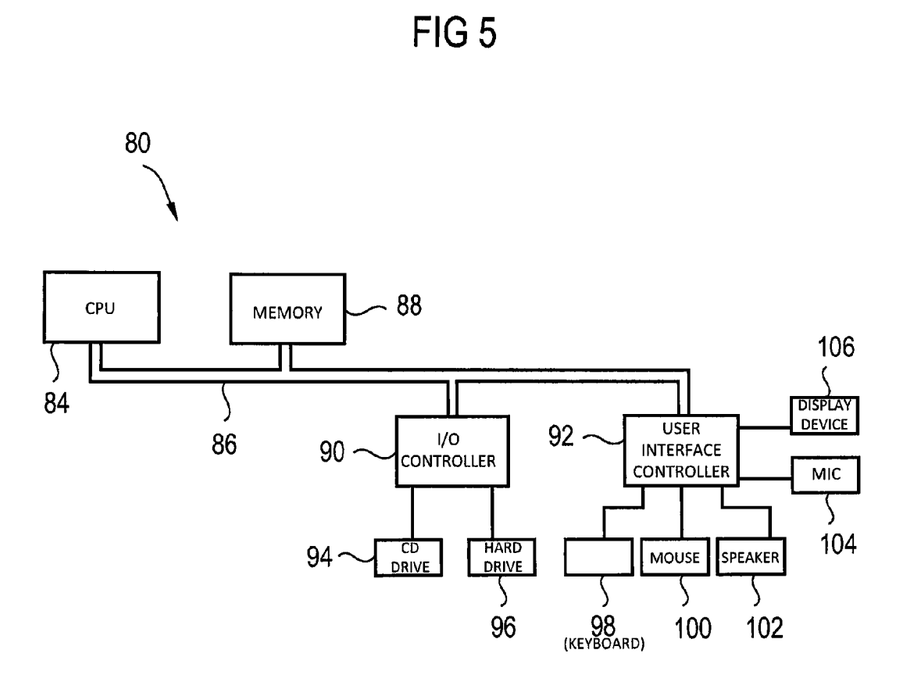
FIG. 5 depicts a representative hardware environment for practicing the embodiments described herein.

FIG. 5 depicts a representative hardware environment for practicing the embodiments described herein. This schematic drawing illustrates a hardware configuration of an information handling/computer system 80 in accordance with the embodiments herein. The system 80 comprises at least one processor or central processing unit (CPU) 84. The CPU 84 is interconnected via bus 86 to various devices such as a memory 88, input/output (I/O) controller 90, and user interface controller 92. Depending on the type and configuration of the system 80, the memory 88 may be volatile (such as random access memory (RAM) etc., non-volatile (read only memory (ROM), flash memory devices etc.) or a combination of the two. The memory 88 is used to store instructions and data for use by the CPU 84. The I/O controller 90 can connect to peripheral devices, such as CD drives 94 and hard drives 96, or other program storage devices that are readable by the system. Typically, an operating system for the computer system 80 as well as an application program is stored onto the hard drive 96. The operating system runs on the CPU 84 and is used to coordinate and provide control of various components within system 80. The system 80 can read the inventive instructions on the hard drive 96 and load them onto the memory 88 for execution by the CPU 84. The user interface controller 92 can connect to a keyboard 98, mouse 100, speaker 102, microphone 104, display device 106 and/or other user interface devices such as a touch screen device (not shown) to the bus 86 to gather user input and also to provide system output to the user.

The embodiments described herein enable reconstructing an emission tomography image in a combined MR and emission tomography imaging system more accurately. Determining, the missing parts of the subject in the MR image enable in obtaining the attenuation which may be induced by the missing parts, and thus, the attenuation of the missing parts may be used with information of the MR image to obtain a correct attenuation model. The correct attenuation model enables in reconstructing the emission tomography image more accurately. Moreover, this eliminates the requirement of using external devices to image the entire profile of the subject.

While this invention has been described in detail with reference to certain preferred embodiments, it should be appreciated that the present invention is not limited to those precise embodiments. Rather, in view of the present disclosure which describes the current best mode for practicing the invention, many modifications and variations would present themselves, to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

10 Combined MR and PET imaging system
15 MR scanner
20 PET subsystem
25 Magnet system
30 Ring
35 Subject
45 Processor
50 Memory
52 MR image
54 CT image
56 Field of View
58 First non perfect emission tomography image
60 First emission tomography image
61' Boosted arm region
61" Boosted arm region
62 Synthetic element
64 Synthetic element
70 Flow diagram block
72 Flow diagram block
74 Flow diagram block
76 Flow diagram block
78 Flow diagram block
80 Computer system
84 Central processing unit
86 Bus
88 Memory
90 I/O Controller
92 User interface controller
94 CD drives
96 Hard drives
98 Keyboard
100 Mouse
102 Speaker
104 Microphone
106 Display device

What is claimed is:

1. A method of reconstructing an emission tomography image in a combined MR (magnetic resonance) and emission tomography imaging system, comprising:
   obtaining an MR image of a subject, the subject being clipped in the MR image;
   obtaining raw emission tomography scan data of the subject;
   determining, using the raw emission tomography scan data, a missing part of the subject clipped in the MR image;
   using information of the MR image and the determined missing part to obtain a final attenuation model of the subject;

reconstructing the emission tomography image using the raw emission tomography scan data and the final attenuation model; and wherein the using of the raw emission tomography scan data to obtain the missing part of the subject includes,
using the raw emission tomography scan data to reconstruct a first emission tomography image with a first attenuation correction model, and
obtaining the missing part from the first emission tomography image.

2. The method according to claim 1, wherein the obtaining of the missing part includes segmenting a profile of the subject reconstructed in the first emission tomography image.

3. The method according to claim 2, wherein the segmentation is performed using a 3d deformable surface model.

4. The method according to claim 1, wherein the first attenuation correction model uses information of the MR image.

5. The method according to claim 1, wherein the first attenuation correction model is solely based on information of the MR image.

6. The method according to claim 1, wherein the first attenuation correction model is based on information of the MR image and a first estimation of the missing part, the first estimation of the missing part being independent from the raw emission tomography scan data.

7. The method according to claim 6, further comprising using the first emission tomography image to adapt synthetic data to the profile of the subject in the MR image.

8. The method according to claim 7, wherein the synthetic data is a phantom data.

9. A non-transitory computer readable medium including program segments for, when executed on a computer device, causing the computer device to implement the method of claim 1.

10. A combined MR (magnetic resonance) and emission tomography imaging system, comprising:
an MR scanner to obtain an MR image of a subject, the subject being clipped in the MR image;
an emission tomography scanner to obtain raw emission tomography scan data of the subject; and
a processor adapted to:
determine, using the raw emission tomography scan data, a missing part of the subject clipped in the MR image,
use information of the MR image and the determined missing part to obtain a final attenuation model of the subject,
reconstruct a final emission tomography image using the raw emission tomography scan data and the final attenuation model, and wherein the processor is further adapted to deter mine the missing part of the subject by using the raw emission tomography scan data to reconstruct a first emission tomography image with a first attenuation correction model, and obtaining the missing part from the first emission tomography image.

11. The system according to claim 10, wherein the processor is configured to obtain the missing part by segmenting a profile of the subject reconstructed in the first emission tomography image.

12. The system according to claim 11, wherein the segmentation is performed using a 3d deformable surface model.

13. The system according to claim 10, wherein the first attenuation correction model uses information of the MR image.

14. The system according to claim 10, wherein the first attenuation correction model is solely based on information of the MR image.

15. The system according to claim 10, wherein the first attenuation correction model is based on information of the MR image and a first estimation of a missing part, the first estimation of the missing part being independent from the raw emission tomography scan data.

16. The system according to claim 15, wherein the processor is configured to use the first emission tomography image to adapt synthetic data to the profile of the subject in the MR image.

17. The system according to claim 16, wherein the synthetic data is a phantom data.

18. A combined MR (magnetic resonance) and emission tomography imaging system, comprising:
means for obtaining an MR image of a subject, the subject being clipped in the MR image;
means for obtaining raw emission tomography scan data of the subject;
means for determining, using the raw emission tomography scan data, a missing part of the subject clipped in the MR image;
means for using information of the MR image and the determined missing part to obtain a final attenuation model of the subject; and
means for reconstructing the emission tomography image using the raw emission tomography scan data and the final attenuation model
wherein the means for determining includes,
means for using the raw emission tomography scan data to reconstruct a first emission tomography image with a first attenuation correction model, and
means for obtaining the missing part from the first emission tomography image.

* * * * *